United States Patent
Sanghvi et al.

(10) Patent No.: US 9,907,982 B2
(45) Date of Patent: Mar. 6, 2018

(54) METHOD OF DIAGNOSIS AND TREATMENT OF TUMORS USING HIGH INTENSITY FOCUSED ULTRASOUND

(71) Applicants: ALBERT EINSTEIN COLLEGE OF MEDICINE, INC., Bronx, NY (US); SONACARE MEDICAL, LLC, Charlotte, NC (US)

(72) Inventors: Narendra T. Sanghvi, Indianapolis, IN (US); Chandan Guha, Scarsdale, NY (US); Russell James Fedewa, Shaker Heights, OH (US); Roy Francis Carlson, New Palestine, IN (US); Ralf Seip, Carmel, NY (US); Wo-Hsing Chen, Fishers, IN (US)

(73) Assignees: Albert Einstein College of Medicine, Inc., Bronx, NY (US); Sonacare Medical, LLC, Charlotte, NC (US)

( * ) Notice: Subject to any disclaimer, the term of this patent is extended or adjusted under 35 U.S.C. 154(b) by 0 days.

(21) Appl. No.: 15/279,514

(22) Filed: Sep. 29, 2016

(65) Prior Publication Data
US 2017/0014651 A1    Jan. 19, 2017

Related U.S. Application Data

(63) Continuation of application No. 14/484,826, filed on Sep. 12, 2014, now Pat. No. 9,457,202, which is a
(Continued)

(51) Int. Cl.
*A61B 8/00*   (2006.01)
*A61N 7/02*   (2006.01)
(Continued)

(52) U.S. Cl.
CPC ............... *A61N 7/02* (2013.01); *A61B 8/08* (2013.01); *A61B 8/0833* (2013.01); *A61B 18/04* (2013.01);
(Continued)

(58) Field of Classification Search
CPC ............. A61N 7/02; A61N 2007/0073; A61N 2007/0004; A61N 2007/0082;
(Continued)

(56) References Cited

U.S. PATENT DOCUMENTS 4,084,582 A   4/1978 Nigam
4,207,901 A   6/1980 Nigam
(Continued)

FOREIGN PATENT DOCUMENTS

CA   1332441   10/1994
CA   2250081   10/1997
(Continued)

OTHER PUBLICATIONS

Dittmar et al., "Pulsed High-Intensity Focused Ultrasound Enhances Systemic Administration of Naked DNA in Squamous Cell Carcinoma Model: Initial Experience" Radiology, 235 (2): p. 541-546, 2005.
(Continued)

*Primary Examiner* — Sanjay Cattungal
(74) *Attorney, Agent, or Firm* — Amster, Rothstein & Ebenstein LLP

(57) ABSTRACT

A method of diagnosis and treatment of tumors using High Intensity Focused Ultrasound is provided. The method of diagnosing the presence of a tumor in a patient comprises the steps of subjecting a tumor to high intensity focused ultrasound (HIFU) to cause the tumor cells to release cellular material and evaluating the cellular material for a tumor marker. The method of treating a tumor in a patient can also
(Continued)

comprise the step of subjecting a tumor to high intensity focused ultrasound (HIFU) to provoke an immune response.

11 Claims, 20 Drawing Sheets

Related U.S. Application Data continuation of application No. 13/571,644, filed on Aug. 10, 2012, now abandoned, which is a continuation of application No. 12/313,665, filed on Nov. 21, 2008, now abandoned.

(60) Provisional application No. 60/989,629, filed on Nov. 21, 2007.

(51) Int. Cl.
| | | |
|---|---|---|
| *A61B 8/08* | (2006.01) | |
| *A61B 18/04* | (2006.01) | |
| *A61B 10/00* | (2006.01) | |
| *A61B 17/225* | (2006.01) | |
| *A61N 7/00* | (2006.01) | |

(52) U.S. Cl.
CPC ......... *A61B 10/007* (2013.01); *A61B 10/0051* (2013.01); *A61B 2017/2253* (2013.01); *A61N 2007/0004* (2013.01); *A61N 2007/0073* (2013.01); *A61N 2007/0082* (2013.01)

(58) Field of Classification Search
CPC ......... A61B 18/04; A61B 8/08; A61B 8/0833; A61B 2017/2253; A61B 10/007; A61B 10/0051
USPC .................................................. 600/437–469
See application file for complete search history.

(56) References Cited

U.S. PATENT DOCUMENTS

| | | |
|---|---|---|
| 4,223,560 A | 9/1980 | Glenn |
| 4,227,417 A | 10/1980 | Glenn |
| 4,248,090 A | 2/1981 | Glenn |
| 4,257,271 A | 3/1981 | Glenn |
| 4,317,370 A | 3/1982 | Glenn |
| 4,325,381 A | 4/1982 | Glenn |
| 4,586,512 A | 5/1986 | Do-Huu |
| 4,620,546 A | 11/1986 | Aida |
| 4,658,828 A | 4/1987 | Dory |
| 4,664,121 A | 5/1987 | Sanghvi |
| 4,858,613 A | 8/1989 | Fry |
| 4,951,653 A | 8/1990 | Fry |
| 4,955,365 A | 9/1990 | Fry |
| 5,036,855 A | 8/1991 | Fry |
| 5,054,470 A | 10/1991 | Fry |
| 5,080,102 A | 1/1992 | Dory |
| 5,117,832 A | 6/1992 | Sanghvi |
| 5,149,319 A | 9/1992 | Unger |
| 5,215,680 A | 6/1993 | D'Arrigo |
| 5,219,401 A | 6/1993 | Cathignol |
| 5,247,935 A | 9/1993 | Cline |
| 5,295,484 A | 3/1994 | Marcus |
| 5,316,000 A | 5/1994 | Chapelon |
| 5,391,197 A | 2/1995 | Burdette |
| 5,409,006 A | 4/1995 | Buchholtz |
| 5,443,069 A | 8/1995 | Schaetzle |
| 5,470,350 A | 11/1995 | Buchholtz |
| 5,492,126 A | 2/1996 | Hennige |
| 5,573,497 A | 11/1996 | Chapelon |
| 5,601,526 A | 2/1997 | Chapelon |
| 5,620,479 A | 4/1997 | Diederich |
| 5,630,837 A | 5/1997 | Crowley |
| 5,643,179 A | 7/1997 | Fujimoto |
| 5,676,692 A | 10/1997 | Sanghvi |
| 5,762,066 A | 6/1998 | Law |
| 5,840,031 A | 11/1998 | Crowley |
| 6,685,639 B1* | 2/2004 | Wang ................. A61N 7/02 600/439 |
| 6,685,640 B1 | 2/2004 | Fry |
| 8,057,408 B2* | 11/2011 | Cain ............... A61B 17/22004 601/2 |
| 2002/0193784 A1* | 12/2002 | McHale ............... A61K 41/00 606/27 |
| 2003/0229283 A1* | 12/2003 | Craig ................. A61B 5/6834 600/439 |
| 2005/0240127 A1 | 10/2005 | Seip |
| 2006/0165710 A1* | 7/2006 | Srivastava ......... A61K 38/1709 424/185.1 |
| 2007/0010805 A1* | 1/2007 | Fedewa ................. A61N 7/02 606/27 |
| 2007/0083120 A1* | 4/2007 | Cain ............... A61B 17/22004 600/439 |
| 2010/0069797 A1* | 3/2010 | Cain ............... A61B 17/22004 601/2 |

FOREIGN PATENT DOCUMENTS

| | | |
|---|---|---|
| WO | 2005107601 | 11/2005 |
| WO | 2007008700 | 1/2007 |

OTHER PUBLICATIONS

Uchida et al., Transrectal High Intensity Focused Ultrasound for Treatment of Patients with Stage T1 b-2NOMO Localized Prostate Cancer: A Preliminary Report Japanese Journal of Endourology and ESWL. 16 (1): p. 108-114, 2003.

* cited by examiner

| | "Low energy HIFU Probe" | "High energy HIFU Probe" |
|---|---|---|
| Aperature [mm] | 34 | 34 |
| Focal Length [mm] | 40 | 42 |
| Frequency [MHz] | 1.015 | 4.00 |
| Focal Spot Dimensions [mm] | 27.11 x 3.11 w | 5.81 x 0.731 w |
| Impedance [Ω] | 46Ω - 36° | 68Ω - 9° |
| Other | Black face 2200pF parallel matching Capacitor | White face |

Serum

Tumor Lysate

| | Cone Height [mm] | Tip Height [mm] with 1.02 MHz Transducer | Tip Height [mm] with 4.0 MHz Transducer | Membrane O-Ring Size |
|---|---|---|---|---|
| Short Cylinder | 23.0 | 21.6 | 21.1 | 026 |
| Medium Cone | 33.4 | 31.0 | 30.6 | 021 |
| Tall Cone | 45.5 | 41.3 | 40.8 | 016 |

| | No treatment | Low HIFU | Low+High HIFU | High HIFU |
|---|---|---|---|---|
| CD3 | 26.99±8.03 | 30.79±8.53 | 37.37±1.74 | 34.89±3.65 |
| CD4 | 13.02±4.33 | 15.94±3.75 | 19.66±1.15 | 18.51±1.81 |
| CD8 | 10.55±3.78 | 11.45±3.17 | 14.03±1.08 | 13.30±1.40 |
| CD4/CD8 | 1.24±0.07 | 1.40±0.10 | 1.41±0.17 | 1.39±0.06 |
| CD69 | 5.55±2.82 | 5.77±2.77 | 7.1±4.71 | 5.99±3.01 |
| CD4CD69 | 1.82±0.49 | 2.21±0.62 | 2.76±1.39 | 2.40±0.96 |
| CD8CD69 | 1.14±0.59 | 1.06±0.59 | 1.31±1.00 | 1.26±0.83 |
| CD80 | 5.08±2.10 | 3.99±1.79 | 5.26±0.98 | 2.40±0.23 |
| CD80+CD11c+ | 2.55±0.33 | 1.56±0.65 | 1.75±0.19 | 1.05±0.05 |
| CD11c | 16.74±1.54 | 13.93±0.50 | 13.51±1.02 | 16.11±1.87 |
| CD11c+NK1.1+ | 10.48±1.31 | 9.68±0.55 | 9.91±1.52 | 12.47±1.59 |
| CD11c+B220+ | 2.21±0.19 | 1.91±0.47 | 1.69±0.19 | 1.92±0.45 |

Figure 18

|  | "Low" energy HIFU Probe | "High" energy HIFU Probe |
|---|---|---|
| Aperture [mm] | 34 | 34 |
| Focal Length [mm] | 40 | 42 |
| Frequency [MHz] | 1.015 | 4.00 |
| Focal Spot Dimensions [mm] | 27.1 l x 3.11 w | 5.8 l x 0.73 w |
| Impedance [Ω] | 46Ω - 36° | 68Ω - 9° |
| Other | Black face<br>2200pF parallel matching Capacitor | White face |

Figure 19

|  | No treatment | Low HIFU | Low+High HIFU | High HIFU |
|---|---|---|---|---|
| CD3 | 26.99±8.03 | 30.79±8.53 | 37.37±1.74 | 34.89±3.65 |
| CD4 | 13.02±4.33 | 15.94±3.75 | 19.66±1.15 | 18.51±1.81 |
| CD8 | 10.55±3.78 | 11.45±3.17 | 14.03±1.08 | 13.30±1.40 |
| CD4/CD8 | 1.24±0.07 | 1.40±0.10 | 1.41±0.17 | 1.39±0.06 |
| CD69 | 5.55±2.82 | 5.77±2.77 | 7.1±4.71 | 5.99±3.01 |
| CD4CD69 | 1.82±0.49 | 2.21±0.62 | 2.76±1.39 | 2.40±0.96 |
| CD8CD69 | 1.14±0.59 | 1.06±0.59 | 1.31±1.00 | 1.26±0.83 |
| CD80 | 5.08±2.10 | 3.99±1.79 | 5.26±0.98 | 2.40±0.23 |
| CD80+CD11c+ | 2.55±0.33 | 1.56±0.65 | 1.75±0.19 | 1.05±0.05 |
| CD11c | 16.74±1.54 | 13.93±0.50 | 13.51±1.02 | 16.11±1.87 |
| CD11c+NK1.1+ | 10.48±1.31 | 9.68±0.55 | 9.91±1.52 | 12.47±1.59 |
| CD11c+B220+ | 2.21±0.19 | 1.91±0.47 | 1.69±0.19 | 1.92±0.45 |

Figure 20

METHOD OF DIAGNOSIS AND TREATMENT OF TUMORS USING HIGH INTENSITY FOCUSED ULTRASOUND

CROSS REFERENCE TO RELATED APPLICATIONS

The present application is a continuation of U.S. application Ser. No. 14/484,826, filed Sep. 12, 2014, now allowed, which is a continuation of U.S. application Ser. No. 13/571,644, filed Aug. 10, 2012, now abandoned, which is a continuation of U.S. application Ser. No. 12/313,665, filed Nov. 21, 2008, now abandoned, which claims the benefit of U.S. Provisional Application No. 60/989,629, filed Nov. 21, 2007, the entire contents of which are incorporated herein by reference, including any references cited therein.

FIELD OF THE INVENTION

The present invention relates to an apparatus and methods for the non-invasive diagnosis and/or treatment of diseased tissue. In particular, the present invention relates to an apparatus and related methods for the non-invasive diagnosis and/or treatment of tumors and metastatic cancer with High Intensity Focused Ultrasound (HIFU).

BACKGROUND

Diseased tissue, such as a cancerous tumor, is commonly diagnosed by taking a biopsy of the tissue for pathology. The biopsy procedure, however, is invasive and involves the removal of a portion of the tissue for analysis. Clearly, it is much more desirable to have a non-invasive method for such diagnosis.

One approach to the treatment of diseased tissue, particularly tumors, is surgical removal. Surgical removal, however, is invasive and can be quite complex and time consuming. Additionally, surgical treatment requires the selective treatment of each individual diseased tissue. Surgical treatment can also result in serious complications, such as from anesthesia. Clearly, a more comprehensive and non-invasive treatment of similar or better efficacy than surgical removal is desirable.

High Intensity Focused Ultrasound (HIFU) has been demonstrated to be a safe modality to treat diseased tissue noninvasively. For example, HIFU has been used to treat prostrate cancer, kidney cancer, and testicular cancer. An exemplary system used to administer HIFU is the Sonablate® 500 (SB500) system available from Focus Surgery, located at 3940 Pendleton Way, Indianapolis, Ind. 46226.

Further exemplary embodiments of systems used to administer HIFU are disclosed in U.S. Patent Publication No. US2007/0010805, filed Jul. 8, 2006, titled "Method and Apparatus for Treatment of Tissue;" U.S. Patent Application Publication No. US 2005/0240127, filed Mar. 2, 2005, titled "Ultrasound Phased Arrays;" U.S. Provisional Patent Application Publication No. US2008/0091123, filed May 6, 2004, titled "Treatment of Spatially Oriented Disease with a Single Therapy, Imaging, and Doppler Ultrasound Transducer;" PCT Patent Application Serial No. US2005/015648, filed May 5, 2005, designating the US, titled "Method and Apparatus for the Selective Treatment of Tissue;" U.S. Pat. No. 4,084,582; U.S. Pat. No. 4,207,901; U.S. Pat. No. 4,223,560; U.S. Pat. No. 4,227,417; U.S. Pat. No. 4,248,090; U.S. Pat. No. 4,257,271; U.S. Pat. No. 4,317,370; U.S. Pat. No. 4,325,381; U.S. Pat. No. 4,586,512; U.S. Pat. No. 4,620,546; U.S. Pat. No. 4,658,828; U.S. Pat. No. 4,664,121; U.S. Pat. No. 4,858,613; U.S. Pat. No. 4,951,653; U.S. Pat. No. 4,955,365; U.S. Pat. No. 5,036,855; U.S. Pat. No. 5,054,470; U.S. Pat. No. 5,080,102; U.S. Pat. No. 5,117,832; U.S. Pat. No. 5,149,319; U.S. Pat. No. 5,215,680; U.S. Pat. No. 5,219,401; U.S. Pat. No. 5,247,935; U.S. Pat. No. 5,295,484; U.S. Pat. No. 5,316,000; U.S. Pat. No. 5,391,197; U.S. Pat. No. 5,409,006; U.S. Pat. No. 5,443,069, U.S. Pat. No. 5,470,350, U.S. Pat. No. 5,492,126; U.S. Pat. No. 5,573,497, U.S. Pat. No. 5,601,526; U.S. Pat. No. 5,620,479; U.S. Pat. No. 5,630,837; U.S. Pat. No. 5,643,179; U.S. Pat. No. 5,676,692; U.S. Pat. No. 5,840,031; U.S. Pat. No. 5,762,066; U.S. Pat. No. 6,685,640; U.S. Abandoned patent application Ser. No. 07/840,502 filed Feb. 21, 1992; Australian Patent No. 5,732,801; Canadian Patent No. 1,332,441; and Canadian Patent No. 2,250,081 (collectively the "HIFU Patents"), the disclosures of all of which are expressly incorporated herein by reference in their entireties.

SUMMARY OF THE INVENTION

The present invention provides a method for diagnosing the presence of a tumor in a patient. The tumor is subjected to HIFU to cause the tumor cells to release cellular material. The cellular material comprises at least one tumor marker. Biological fluid obtained from the patient is then evaluated to determine the presence and/or level of the tumor marker in the fluid. Preferably, the biological fluid is blood, urine or saliva.

The invention also provides a method of treating a malignant tumor in a patient. HIFU is delivered to the tumor to cause the tumor cells to release cellular material that provokes an immune response. In one embodiment, the patient's immune response to the tumor cells is amplified by using one or more immunotherapy techniques.

In an alternative embodiment, the invention provides a method of treating metastatic cancer in a patient, where the cancer arises from at least one malignant tumor in the patient. HIFU is delivered to the tumor, and the HIFU causes the release of cellular material from tumor cells within the tumor, thus provoking an immune response that encompasses some or all of the metastatic cells. In one embodiment, the patient's immune response to the tumor cells is stimulated by using one or more immunotherapy techniques.

In yet another alternative embodiment, the invention provides a method for treating tumors that are not agitated by HIFU treatment. HIFU is delivered to a tumor, wherein the HIFU causes the release of cellular material that provokes an immune response to treat the unagitated tumors.

However, persons skilled in the art will be able to apply the apparatus and methods of the invention to human patients and to non-human mammals, such as laboratory mice and rats, dogs, cats, horses, and primates, for research, diagnostic, or treatment purposes.

Additional features of the present invention will become apparent to those skilled in the art upon consideration of the following detailed description of the illustrative embodiments exemplifying the best mode of carrying out the invention as presently perceived.

As used herein, the term "tumor marker" is any detectable molecule from a tumor in a mammal that indicates the presence of the tumor in the mammal.

BRIEF DESCRIPTION OF THE DRAWINGS

The detailed description of the drawings particularly refers to the accompanying figures in which:

FIG. 18 shows phenotype of splenocytes and levels of heat shock protein after HIFU treatment.

FIG. 19 shows the characteristics of the acoustic probes attached to the HIFU driving system.

FIG. 20 shows the phenotype of splenocytes and levels of heat shock proteins after HIFU treatment.

DETAILED DESCRIPTION OF THE INVENTION

Figure 1:
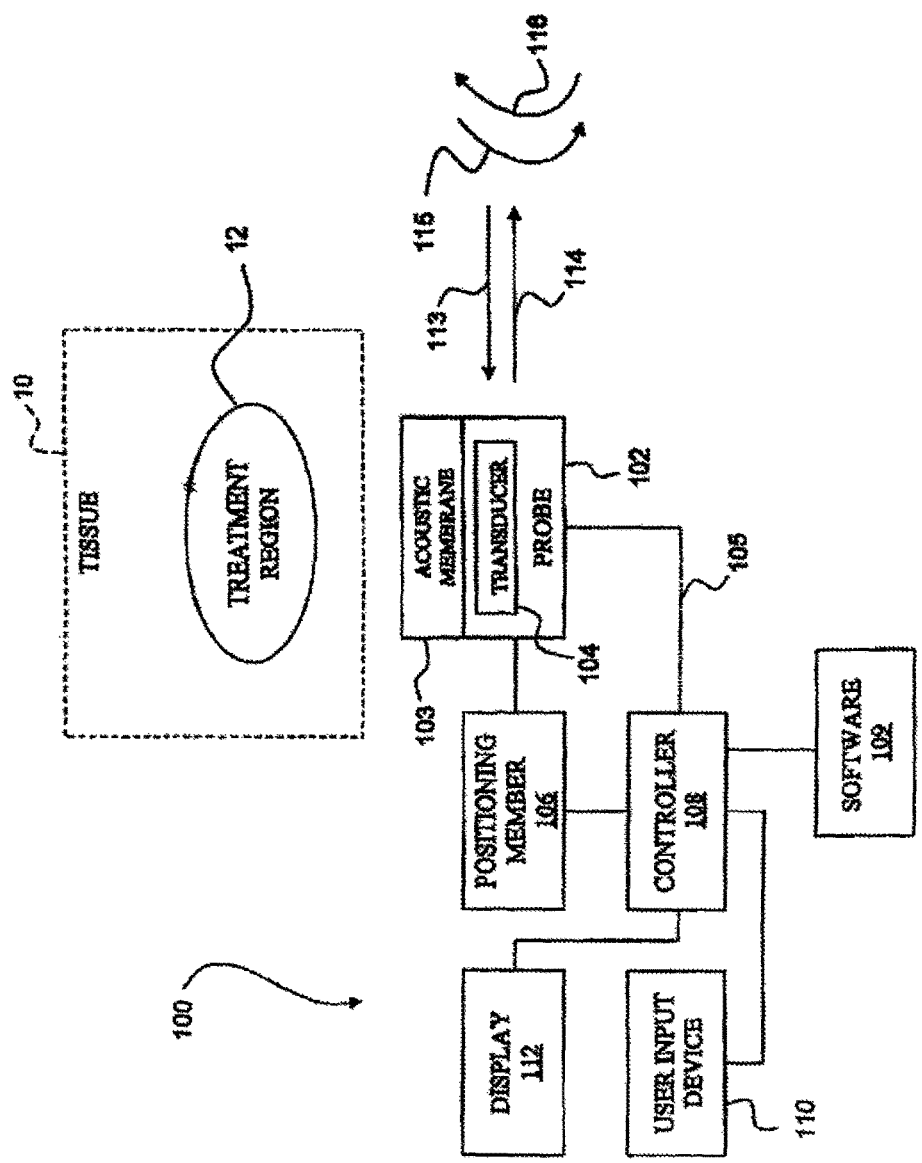
FIG. 1 is schematic view of an exemplary HIFU System.

The application of energy to a targeted region (e.g. HIFU, cryoablation, ionizing radiation, radiofrequency ablation, laser ablation, etc.) is separated into two types: high energy treatment and low energy treatment.

High energy treatment is defined as a treatment with the goal of necrosis or ablation of the targeted tissue. An example of a high energy treatment is high energy HIFU (HI-HIFU). HI-HIFU typically applies 3.1 to 9.1 KW-sec of energy per $cm^2$, though intensities higher and lower than this range can be used. HI-HIFU typically operates with a continuous wave applied for a duration in the range of 3 to 20 seconds and with an operating frequency range between 1 and 5 MHz, though longer and shorter durations can be used with higher or lower operation frequencies. When HI-HIFU is used to cause extensive or essentially complete necrosis, the frequency of the HIFU can be greater than about 20 KHz and less than about 100 MHz. An example of a HI-HIFU treatment is the complete ablation of the prostate using HI-HIFU with the result of the entire prostate experiencing coagulative necrosis.

In contrast, low energy treatment is defined as a treatment with energy levels such that the targeted tissue is agitated but remains viable. An example of a low energy treatment is low energy HIFU (LO-HIFU). Since pulsing is a way of modulating power, LO-HIFU can be accomplished by pulsing of a HI-HIFU source. LO-HIFU can be accomplished by moving a HIFU transducer to move the focus of the HIFU. In one embodiment HI-HIFU is swept across the targeted tissue to accomplish LO-HIFU. LO-HIFU typically applies 0.01 to 1.0 KW-sec of energy per $cm^2$, though intensities higher and lower than this range can be used. LO-HIFU, when applied in a pulsed manner, operates with a pulse duration in the 1 to 100 millisecond range with pulse repetition frequencies in the range between 0.5 to 5.0 Hz, though longer and shorter pulse durations can be used with higher or lower repetition frequencies. In one embodiment, LO-HIFU operates with a repetition frequency in the range between 0.5 to 30 Hz. An example of a LO-HIFU treatment is the application of LO-HIFU in order to disturb the blood-brain barrier to permit the passage of drugs from the blood stream into the brain.

The application of the treatment described in this invention may occur using invasive, minimally invasive, and non-invasive approaches. The probes used for applying the energy may be extracorporeal, intra-cavity, percutaneous, or applied in an open surgery. These probes may be applied by manual/direct position with image guidance (e.g. visual, video, ultrasound, MRI, etc.), by robotic means with image guidance, or by some combination of manual/direct and robotic. An exemplary type of treatment is HIFU which is capable of delivering both "high" and "low" energy to a targeted region. An example is a HIFU probe introduced laparoscopically to treat (with "low" or "high" energy) a renal tumor that is guided by both video feedback using the image provided by the laparoscope as well as ultrasound guided using the mechanically controlled (robotic) ultrasound transducer within the HIFU probe.

An exemplary HIFU System 100 is shown in FIG. 1. HIFU System 100 includes a probe 102 having a transducer member 104, a positioning member 106, a controller 108 operably coupled to probe 102 and the positioning member 106, a user input device 110 (such as keyboard, trackball, mouse, and/or touch screen), and a display 112. Probe 102 is operably connected to controller 108 through positioning member 106. However, as indicated by line 105 probe 102 may be directly connected with controller 108. Positioning member 106 is configured to linearly position transducer member 104 along directions 113, 114 and to angularly position transducer member 104 in directions 115, 116. Further details of suitable HIFU systems used in the treatment of tissue which may be modified to execute the methods described here are provided in the HIFU Patents. In one embodiment, HIFU System 100 is configured to both image tissue and to treat tissue.

In one embodiment, HIFU System 100 is configured to provide a HI-HIFU treatment. A HI-HIFU treatment includes the administration of acoustic energy in a manner that causes generally instantaneous thermally induced coagulative necrosis of the targeted tissue. For example, HI-HIFU treatment is administered as a continuous wave having a duration of about 3 seconds, an operating frequency of about 4 MHz, and approximate focal spatial peak temporal peak (SPTP) intensities of about 1.3 to about 2.0 $KW/cm^2$, resulting in tissue temperatures in the focal zone of about 80° C. to about 95° C.

In another embodiment, HIFU System 100 is configured to provide a LO-HIFU treatment. A LO-HIFU treatment includes the administration of acoustic energy in a manner that causes a membrane of a cell to be disrupted while maintaining cell viability and avoiding cavitation. LO-HIFU treatment enables DNA and other molecules to pass through the cell membrane as discussed in the article by K M Dittmar, J Xie, F Hunter, C Trimble, M Bur, V Frenkel, and K C P Li, titled "Pulsed High-Intensity Focused Ultrasound Enhances Systemic Administration of Naked DNA in Squamous Cell Carcinoma Model: Initial Experience" Radiology. 235 (2): p. 541-546, 2005, the disclosure of which is expressly incorporated by reference herein in its entirety. In one example, LO-HIFU treatment is administered as a series of short pulses of acoustic energy with a pulse duration in the range of micro-seconds to milli-seconds (pulse repetition rate of about 1 Hz), approximate focal spatial peak temporal peak intensities of about 0.5 $KW/cm^2$, and an operating frequency of about 1 MHz.

In one embodiment, HIFU System 100 is configured to selectively provide both a HI-HIFU treatment and a LO-HIFU treatment. In one embodiment, HIFU System 100 includes a pre-programmed setting for each of a HI-HIFU treatment and a LO-HIFU treatment such that the user selects a target tissue by methods explained in the HIFU Patents previously referenced.

The exemplary HIFU System 100 is capable of applying HIFU through an extracorporeal probe, an intra-cavity probe, a laparoscopic probe, or a probe designed for open surgery. The probe may be placed directly on the target tissue.

Figure 5:
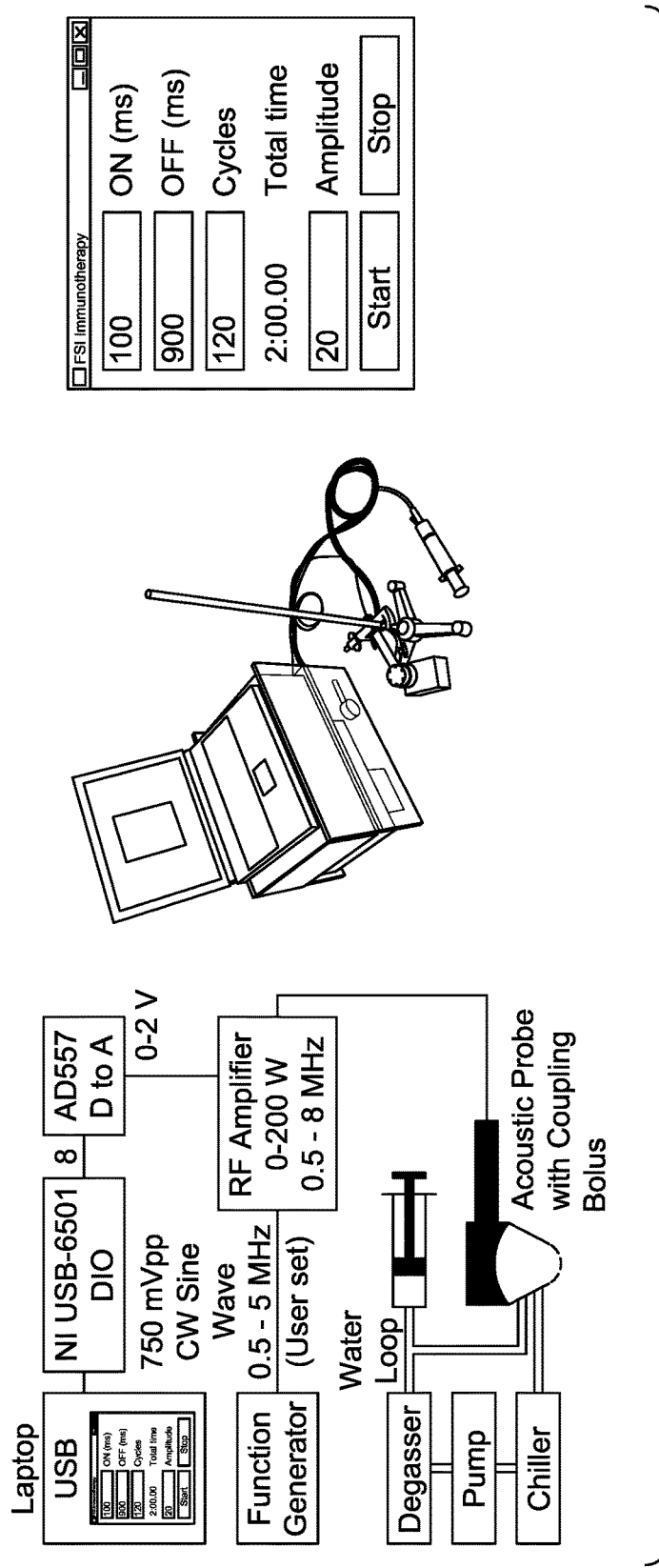
FIG. 5 is a representation of the developed HIFU driving system to drive the LO-HIFU and HI-HIFU.
Figure 6:
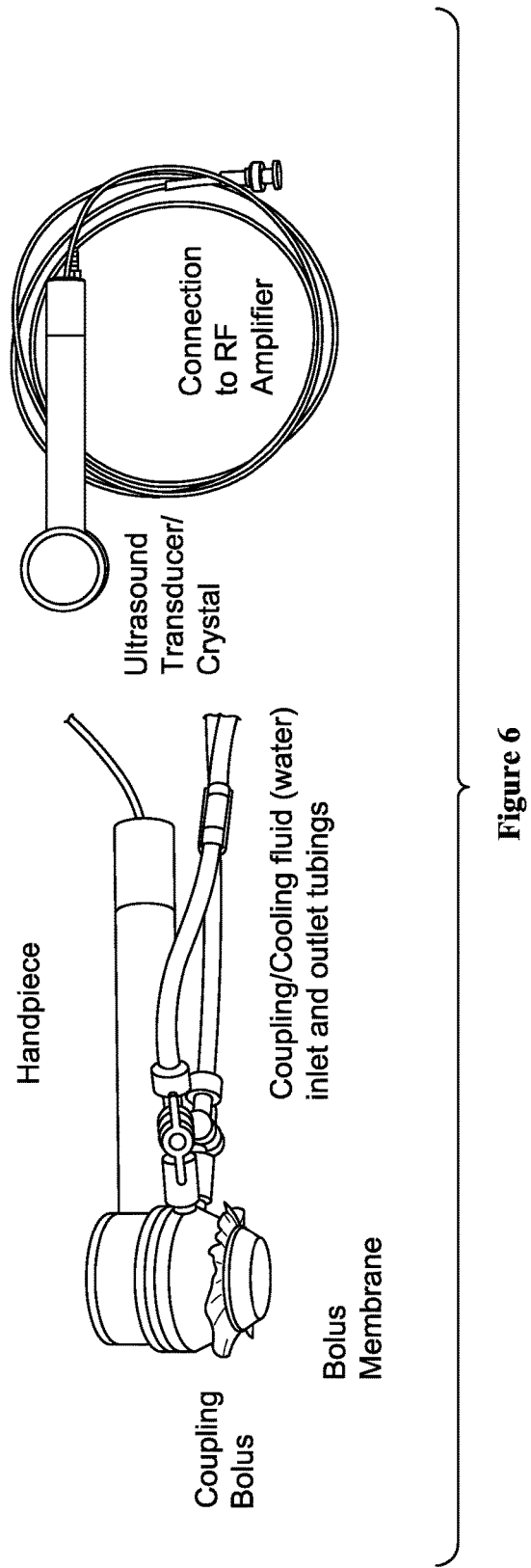
FIG. 6 shows acoustic probes capable of delivering LO-HIFU and HI-HIFU.

An exemplary HIFU driving system is shown in FIG. 5. The main goal of this driving system is to provide a general-purpose, easy-to-use, compact, and portable system for delivering HIFU. The system has an operating frequency in the range of about 0.5 to 30 Hz, a minimum focal intensity of about 0.5 $KW/cm^2$ for LO-HIFU probes, and a minimum focal intensity of about 2.0 $KW/cm^2$ for HI-HIFU probes. The driving system has a minimum "on" time of about 0.05 seconds and a maximum "on" time of about 30 seconds. The driving system has a minimum "off" time of about 0.05 seconds and a maximum "off" time of about 30 seconds. The controls for the "on" time and the "off" time are programmable.

The driving electronics for the HIFU driving system consist of a signal generator, RF amplifier, water circulation pump with a solid-state liquid-to-air chiller, inline water degassing system, and bolus volume adjustment for probe cooling and coupling, a USB-based computer/amplifier interface, and a laptop computer for HIFU on/off and power control, all housed in one unit.

Figure 17:
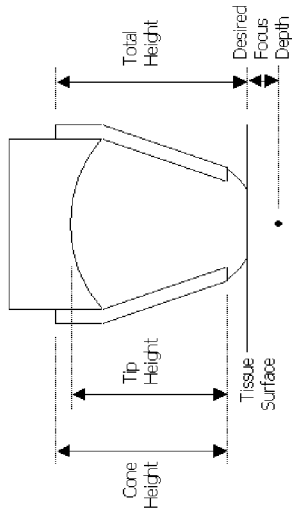
FIG. 17 shows the general configuration of a coupling cone.

The acoustic probes attached to the HIFU driving system are shown in FIG. 5. The HI-HIFU acoustic probes in the driving system were configured to have an operating frequency of about 4 MHz, and the LO-HIFU acoustic probes in the driving system were configured to have an operating frequency of about 1 MHz. Both the HI-HIFU acoustic probes and the LO-HIFU acoustic probes were configured to have an F-number of approximately 1. Additional characteristics of these probes are shown in FIG. 17.

Coupling boli ("cones") of different heights were also constructed that are attached to the front of the probe, so as to allow for transducer cooling, transducer/tissue coupling, and focal zone placement at a desired depth. The cones are closed on one end with an acoustically transparent latex membrane. In one embodiment, the cones are made from poly-methyl methacrylate (PMMA), though any similar material may be used.

The general configuration of the cone characteristics are shown in FIG. 19.

The following relationship was used to choose the cone and adjust the bolus height for placing the transducer focal spot at a desired depth:

$$\text{Total Height} = \text{Focal Length} + \text{Cone Height} - \text{Tip Height} - \text{Desired Focus Depth}$$

In the examples described herein, the tall cones were used throughout. With a desired focus depth of 0 to −2 mm, this arrangement allowed the placement of the focal zone of both transducers to be just within the animal tumor and facilitated probe-tip/tumor alignment.

Figure 7:
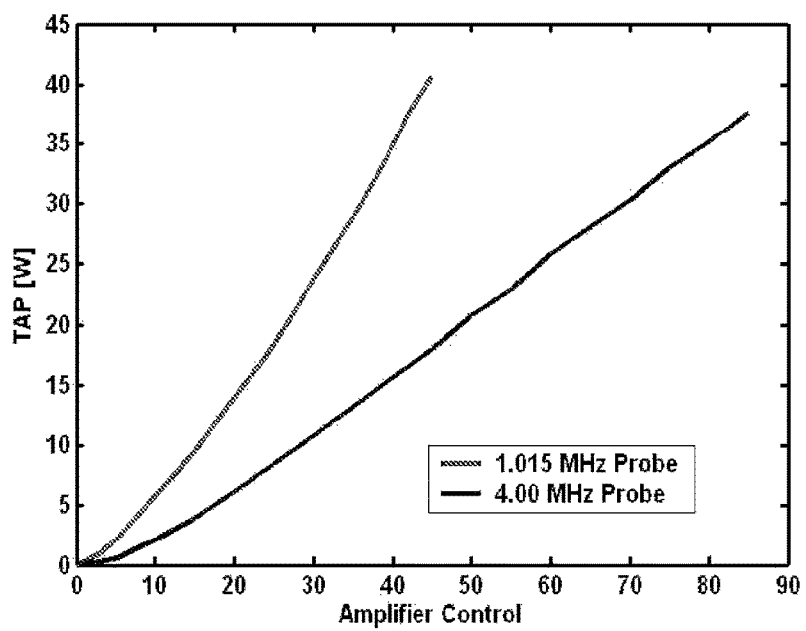
FIG. 7 shows the Total Acoustic Power (TAP) probe output for the acoustic probes when coupled to the developed driving electronics.

The driving electronics, water management system, probes and boli were tested in-vitro with fresh chicken tissue at approximately 30-35° C. The purpose of these tests was also to determine starting operating parameters for the in-vivo experiments with respect to the Total Acoustic Power (TAP, shown in FIG. 7), HIFU on time, HIFU off time, spacing between individual sites, and number of cycles in order to achieve the required intensities and therapeutic effects. For the HI-HIFU probe, these effects mainly included thermal tissue coagulative necrosis using short exposure times (1-5 seconds); for the LO-HIFU probe, these effects mainly included tissue temperature rises of no more than 5° C. to maintain tissue viability while using pulsing sequences.

Figure 8:
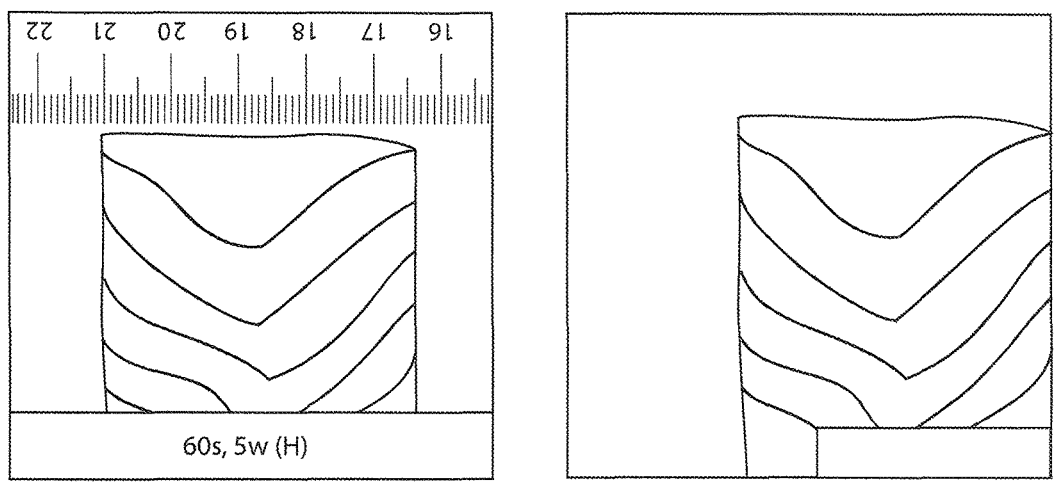
FIG. 8 shows the typical in-vitro result using the HI-HIFU and LO-HIFU probe.

For the HI-HIFU probe, a TAP of 5 W, a HIFU "on" time of 30-60 seconds (1 cycle) and 3-4 mm spacing between adjacent treatment sites resulted in a continguous ablation region and tissue temperatures exceeding 80° C. (FIG. 8). For the LO-HIFU probe, a TAP of 20-40 W, a HIFU "on" time of 0.1 seconds, a HIFU "off" time of about 1 to 60 seconds, 60-120 cycles, and 3 mm spacing between adjacent treatment sites resulted in a tissue temperature rise <10° C. without indication of ablation. These values formed the starting operating parameters for the in-vivo experiments, and were modified as required.

It has been shown that the administration of HI-HIFU treatment to the prostate results in an elevated release of specific antigen levels, in particular PSA, into the bloodstream. Further details are provided in U.S. Patent Application Publication No. US2007/0010805, filed Jul. 8, 2005, titled "METHOD AND APPARATUS FOR TREATMENT OF TISSUE", the disclosure of which is expressly incorporated by reference herein in its entirety, and in the article by T Uchida, H Tsumura, H Yamashita, M Katsuta, D Ishii, T Satoh, A Ohkawa, T Hyodo, and N T Sanghvi, titled "Transrectal High Intensity Focused Ultrasound for Treatment of Patients with Stage T1b-2NOM Localized Prostate Cancer: A Preliminary Report" published in Japanese Journal of Endourology and ESWL. 16(1): p. 108-114, 2003, the disclosure of which is expressly incorporated by reference herein in its entirety.

As explained herein, HIFU may be used to induce the release of heat shock proteins, which stimulate the immune response of the patient. In particular, experiments were conducted with HI-HIFU, which was used to approximate a LO-HIFU treatment.

The invention provides a method of diagnosing the presence of a malignant tumor in a patient. The tumor is subjected to HIFU to cause the tumor cells to release cellular material. The cellular material comprises at least one tumor marker. As used herein, the term "tumor marker" is any detectable molecule from a tumor in a mammal that indicates the presence of the tumor in the mammal. Preferably, the mammal is a human and the tumor marker is a human tumor marker.

A biological fluid from the patient is then evaluated to determine the presence and/or the level of the tumor marker. The presence and/or level of the tumor marker (or the absence thereof) may be determined prior to application of the HIFU and then compared to the presence and/or level of the tumor marker after the application of the HIFU. Preferably, the biological fluid is blood, urine or saliva.

Figure 2:
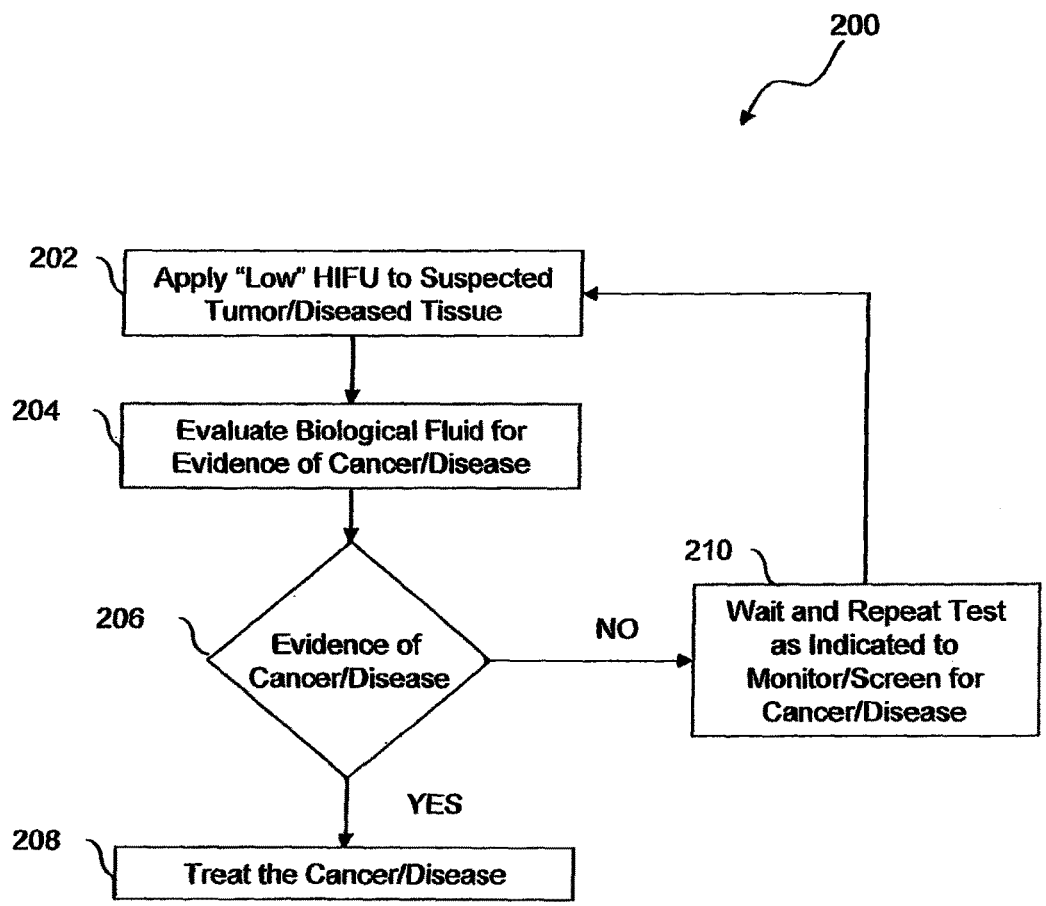
FIG. 2 is an exemplary method of diagnosing diseased tissue with the application of a treatment to agitate or ablate a suspected region of tissue where an example of a system to apply the treatment is the HIFU System of FIG. 1.

Based upon the ability of HIFU to induce the release of material from cells, such as proteins, and other cellular material, HIFU may be used as a generally non-invasive form of evaluating a given tissue for disease, such as cancer. Referring to FIG. 2, a first exemplary method 200 is shown.

In one of the diagnostic aspects of the invention, the HIFU is LO-HIFU. The energy of the LO-HIFU may be adjusted to maintain tumor cell viability.

In another diagnostic aspect of the invention, HI-HIFU is used. This results in at least partial necrosis of the tumor, and often extensive or essentially complete necrosis. When used in this manner, the frequency of the HIFU is greater than about 20 KHz and less than about 100 MHz.

The HIFU may be applied more than once. In a preferred embodiment, LO-HIFU is first applied to the tumor, followed within a time period of two to seven days by HI-HIFU. Alternatively, the LO-HIFU is applied to the tumor, followed within a time period of two to seven days by another LO-HIFU treatment. In yet another alternative, the HI-HIFU is applied to the tumor, followed within a time period of two to seven days by another HI-HIFU treatment. In yet another alternative, a combination of LO-HIFU and HI-HIFU is applied to the tumor, followed within a time period of two to seven days by another combination of LO-HIFU and HI-HIFU.

A baseline measure of the disease marker is obtained prior to application of HIFU to the targeted tissue. As discussed herein, the LO-HIFU or HI-HIFU treatment 202 in FIG. 2 causes the release of cellular materials from the targeted tissue into the bloodstream and potentially into other bodily fluids, such as urine or saliva. Diseased cells, such as malignant cells, contain cellular material that provide an indication of disease either from the presence or the prevalence of the cellular marker in the bodily fluid following the agitation/ablation of the targeted tissue from the treatment 202. Such markers include tumor antigens, tumor markers and heat shock proteins (HSPs). Both HI-HIFU and LO-HIFU treatments may be used to release markers into a bodily fluid. In some instances, LO-HIFU treatment may result in a higher level of such cellular material to be released into the biological fluid by the cells targeted by the LO-HIFU treatment, thereby raising the level of the cellular material in the biological fluid, such as blood, saliva, or urine. In one embodiment, the time between the application of HIFU and the evaluation of the cellular material is 24 to 48 hours. A complete HI-HIFU treatment of the tumor (e.g. total ablation of the prostate using high energy HIFU) quickly destroys the cells and the vascular system and may provide a reduced production and release of disease markers (e.g. HSPs) with a reduced ability to distribute these markers to the bodily fluid of interest in comparison to LO-HIFU. Another instance may use LO-HIFU followed by a partial HI-HIFU treatment of the tumor in order to develop and release markers into the biological fluid.

The evaluation 204, in FIG. 2, of biological fluid determines the presence and/or level of the marker in the fluid. In one embodiment, wherein the biological fluid is blood, a blood sample is drawn from the patient and processed to evaluate the blood by techniques known to those skilled in the art.

Based upon the presence and/or level of the marker in the biological fluid, a determination 206 may be made regarding whether the target tissue is diseased or normal.

Other markers indicate the presence of a condition when their concentration is above or below a certain level. Prostate Specific Antigen (PSA) is an example of such a marker.

Persons skilled in the art are familiar with many markers, and with how they indicate the presence or absence of conditions. The use of them in the diagnostic techniques of this invention is based on this experience with known diagnostic markers, as well as new markers. Such markers are given new and/or enhanced usefulness by the diagnostic techniques of this invention.

If the determination is made that the cells are normal, then a subsequent follow-up test 210 may be scheduled to monitor the status of the tissue.

If the determination is made that the cells are diseased, then appropriate treatment action can be taken, as demonstrated in 208.

The invention also provides a method of treating a malignant tumor in a mammal, preferably a human patient. This method involved stimulating the patient's immune response to malignant tumor cells in the malignant tumor. It is particularly useful in treating metastatic cancer in the patient, where the cancer arises from at least one malignant tumor. The method comprises delivering HIFU to the tumor to cause the tumor cells to release cellular material and amplifying the patient's immune response to the tumor cells by using one or more immunotherapy techniques that utilize the cellular material. The tumor may be any solid tumor. In a preferred embodiment, the tumor is prostate cancer.

The cellular material comprises molecules released from the cell by the HIFU. For example, the molecules may be DNA, RNA, proteins, and peptides. Among the proteins released are heat shock proteins. Certain of these molecules may act as a tumor antigen. As used herein, the term "tumor antigen" is a molecule from a tumor in a mammal that stimulates an immune response in the mammal to the molecule and/or to the tumor cell. Preferably, the mammal is a human and the tumor antigen is a human tumor antigen Various methods may be used to treat the diseased tissue, including HI-HIFU treatment, immunotherapy, chemotherapy, or surgery. In one embodiment, HI-HIFU treatment is used to non-invasively treat the diseased tissue. Exemplary methods of performing HI-HIFU treatment are provided in the HIFU Patents previously referenced, all of which are incorporated herein by reference in their entireties.

Further, based upon the ability of the application of HIFU 202, in FIG. 2, to induce the release of material from cells such as proteins and other antigenic lysates, such treatment may be combined with any immunological therapy or series of immunological therapies to treat diseased tissue.

The HIFU can be applied in any one of the following manners: extracorporeal, intra-cavity, percutaneous, robotic, laparoscopic and directly on the tumor. The HIFU may be applied using intensity modulation and/or frequency modulation.

Figure 3:
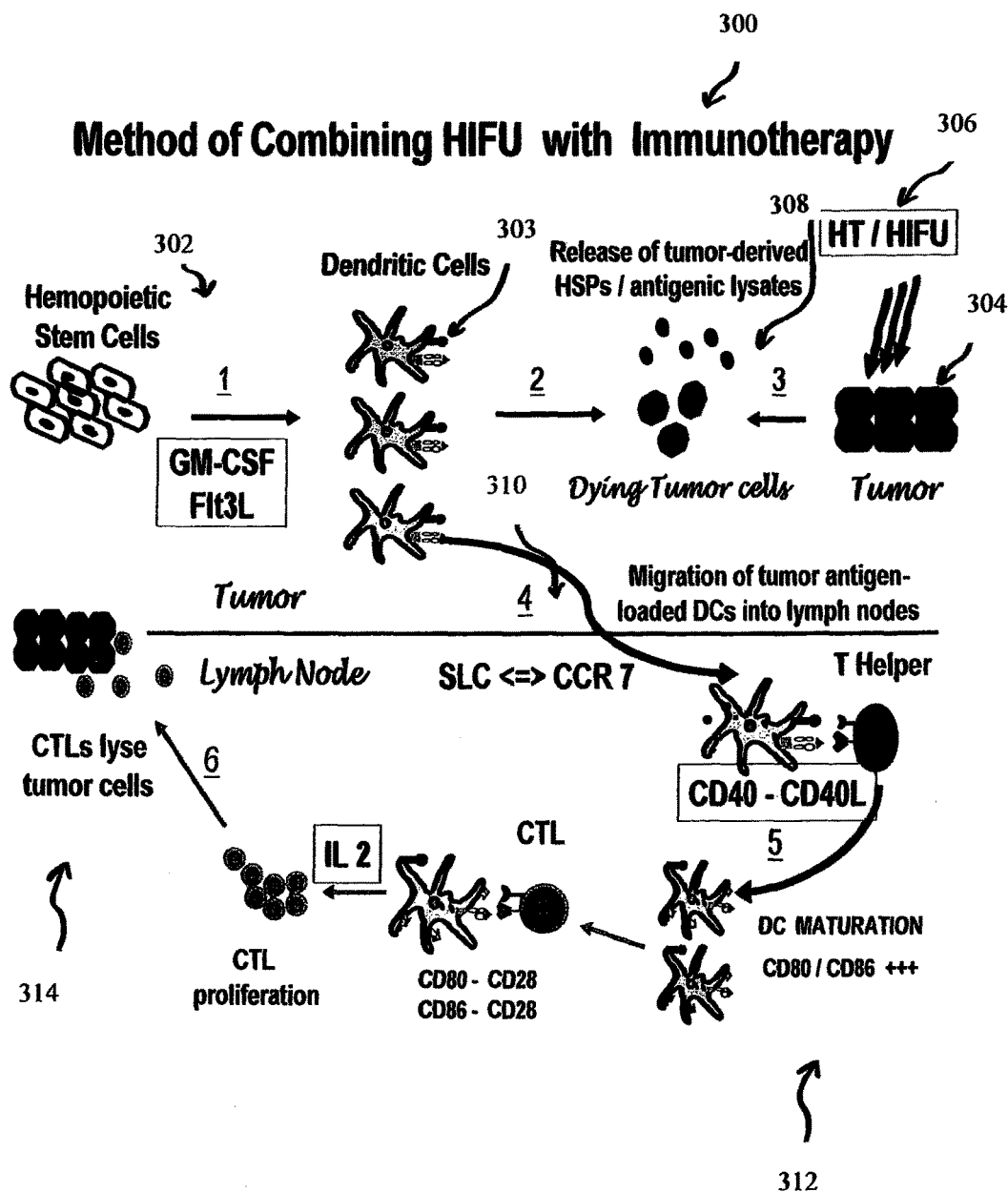
FIG. 3 is an exemplary method of treating a tumor with HIFU and immunotherapy.

HIFU treatment can go beyond treating a targeted tumor and can treat the occurrence of cancer in the tissue surrounding the targeted region or distant metastatic cancer. Referring to FIG. 3, a first exemplary method 300 is proposed for such treatment.

An exemplary integrated Local Energy Application with Immunological Therapy 300 is shown in FIG. 3. As generally represented by area 302, stem cells are stimulated with dendritic cell (DC)-stimulating cytokines to produce DCs 303 in order to prepare the immune system to be receptive to the cellular material disbursed by the HIFU treatment 306. Exemplary DC-stimulating cytokines include G-CSF, GM-CSF and Flt3L. Next, the target tissue 304 is treated with HIFU 306. The target tissue releases cellular material 308, such as heat shock proteins and antigenic lysates.

In one embodiment, the low energy treatment 306 in FIG. 3 is LO-HIFU. Without being bound by theory, the Applicants believe that HIFU induces heat shock proteins (HSPs) in tumor cells, which are released in the blood after HIFU treatment of solid tumors. Since HSPs-bind to intratumoral peptides, spontaneous release of HSPs from HIFU-treated tumor cells should provide a source of tumor antigens for antigen presentation by circulating DCs 303. The cellular material 308 is uptaken by the DCs 303. The tumor antigen-loaded DCs then expected migrate into the lymph nodes as represented by area 310. Furthermore, the HSPs released in the blood after HIFU treatment of tumor cells provide the "danger" signals to the DCs and also to provide a source of comprehensive tumor-derived peptides for efficient antigen presentation.

In the lymph nodes, maturation of the DCs occurs as represented by area 312 in FIG. 3. In one example, CD40L provides signals for DC maturation and thereby eliminates the need of CD4 T cells. Further, in one example, secondary lymphoid chemokines (SLCs) assist in the migration of DCs into draining lymph nodes and interact with T cells to induce a cell-mediated anti-tumoral immunity. Sequential use of T lymphocyte-stimulating cytokines induces a strong immune response. Further, IL-2 amplifies the tumor-specific cytotoxic T lymphocytes and IL-15 induces a strong memory T cell response.

As a result, cytotoxic T lymphocytes (CTLs) proliferate and destroy other tumor cells as represented by area 314 in FIG. 3. Thus, HIFU-treated tumor cells serve as an in situ tumor vaccine and induce a strong tumor-specific immune response to eradicate distant micro-metastases in recurrent solid tumors.

In one embodiment, administration of anti-CTLA4 antibodies after the HIFU treatment down-regulate regulatory T cells, thereby augmenting the tumor-specific immune response. In another embodiment, administration of 4-1BBL enhances the CTL effector and memory T cells. In still another embodiment, a variety of CpG oligonucleotides are used with the HIFU treatment to enhance the innate immunity after treatment. CpG oligonucleotides induce DC maturation and break tolerance to tumor antigens.

Instead of individualized vaccines, treatment 300 in FIG. 3 depends on the endogenous circulating DCs to harvest the tumor antigens released by dying cells after an HIFU treatment. In addition, combining traditional immunotherapy with local tumor high and/or low energy HIFU treatment should at least allow the local energy treatment to reduce the tumor burden without causing generalized immuno-suppression as seen with chemotherapy. Further, the combination should also serve as antigen depot for "boosting" immunological memory and inducing a more extensive immune response by antigen spreading, thereby enhancing the vaccine effect.

The immune response produced by exemplary method 300 in FIG. 3 may be monitored by known techniques. If the immune response is insufficient, the process 300 may be repeated. If the immune response is acceptable and the local disease is insufficiently treated following the previous energy treatment, a high energy HIFU treatment may be applied with or without the immunotherapy steps to address the local disease. The exemplary method 400 shown in FIG. 4 demonstrates the choices following treatment using the immunology with energy application treatment.

Figure 4:
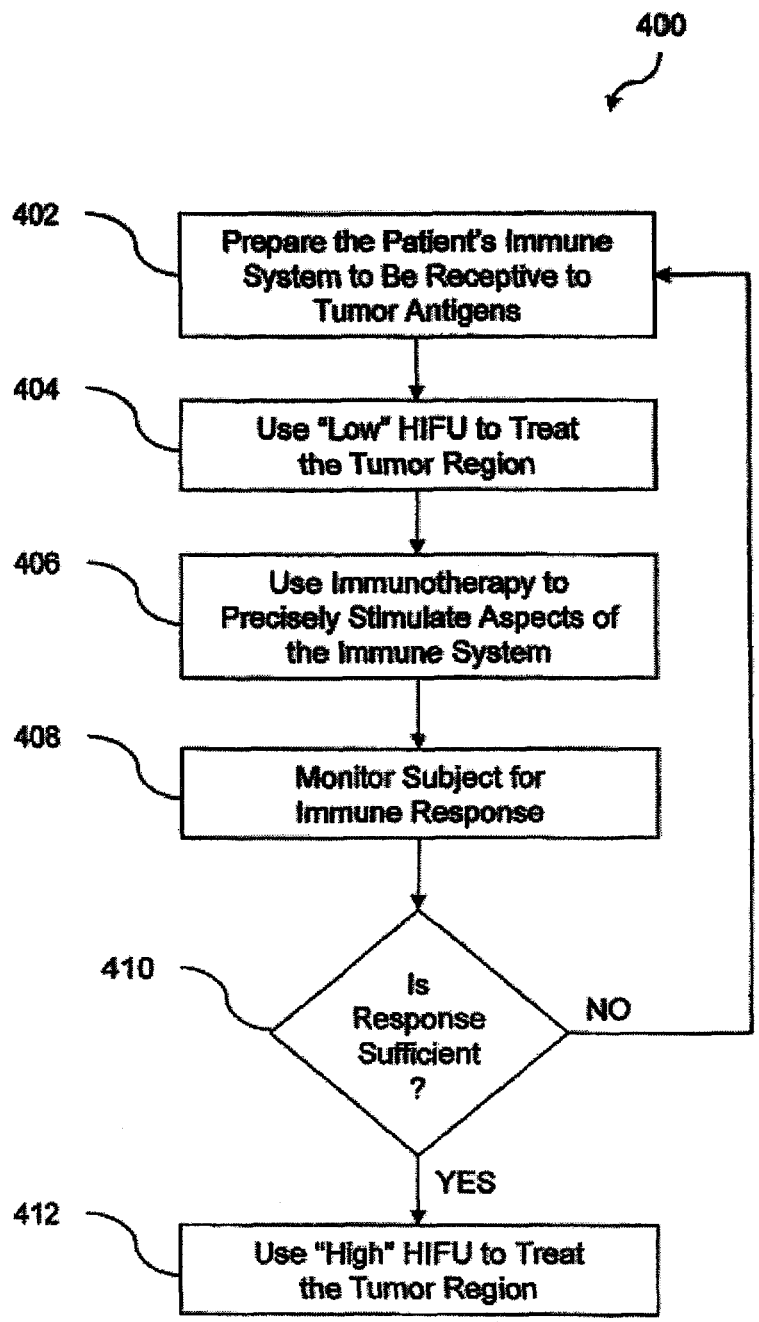
FIG. 4 is another exemplary method of treating a tumor with HIFU and immunotherapy.

As represented by 402 in FIG. 4, the patient's immune system is prepared to be receptive to tumor antigens. Exemplary preparation is the use of cytokines to stimulate the production of dendritic cells. The tumor region, such as the prostate, is subjected to LO-HIFU treatment 404. As an alternative, the tumor region can be subjected to HI-HIFU or to a combination of LO-HIFU and HI-HIFU. The treatment releases cellular material from the tumor cells, including heat shock proteins and antigenic lysates. One or more immunotherapy techniques 406 are applied to precisely stimulate the immune system response.

As represented by 408, the immune response of the patient is monitored. If the immune response is unacceptable, the process 400 may be repeated. If the immune response is sufficient and the local disease is fully treated, then no additional treatment is needed. If the immune response is sufficient but the local disease is not fully treated, then a high energy HIFU treatment 412 is applied to completely ablate the tumor and may be repeated if local disease recurs.

The immunotherapy technique may be applied more than once. It may be applied before or after the HIFU treatment.

In one embodiment of the invention, the immunotherapy technique comprises delivering to the mammal an effective amount of the composition that stimulates the immune system of the mammal. The composition may be an anti-tumor vaccine, such as an autologous tumor cell vaccine.

Alternatively, the composition is an immunomodulatory molecule. Preferably, the molecule is a cytokine. Such cytokines include, but are not limited to, lymphokines, interleukins and chemokines. In one aspect of the invention, the cytokine is a dendritic cell-stimulating cytokine. These include G-CSF, GM-CSF, IL-4, and FIt3L.

In another embodiment of the invention, the immune response provoked by the use of HIFU is enhanced by the administration of compositions which cause the body to have a stronger immune response. These immune boosting compositions are known in the art, although their use in the context of HIFU treatments is novel. Examples of these compositions include cytokines, such as lymphokines and chemokines. Preferably, these are dendritic cell stimulating cytokines.

These immune boosting compositions include G-CSF, GM-CSF, IL-4, and Fit3L. A number of suitable immune boosting compositions are available commercially and are already approved for use in humans, though not yet approved for use in this context. For example, Leukine is a GM-CSF product available from Berlex Laboratories. Neupogen is recombinant methionyl human granulocyte colony-stimulating factor (r-metHuG-CSF) available from Amgen. Neulasta is a covalent conjugate of recombinant methionyl human G-CSF and monomethoxypolyethylene glycol and is also available from Amgen. Proleukin is IL-2, and is available from Novartis. Other useful immune boosting compositions include IL-2, IL-I-5, CD40L, 4-1 BB ligand, or a CpG oligonucleotide. In still another aspect of the invention, the immunomodulatory molecule is a molecule that down-regulates regulatory T-cells. These molecules include an anti-CTLA4 antibody.

These and other immune boosting compositions are effective in enhancing the immune response provoked by use of HIFU according to the present invention. Techniques for their safe use is well known to those skilled in the cancer therapy field. The specific dose of each of these compositions which is used in a particular patient is a matter for the well-informed clinician's professional judgment based on well established factors including body weight, prior status of the patient's immune system, and the closely monitored response of the patient to the composition. This same judgment, operating within these well established clinical parameters, applies when the immune boosting compositions are used as part of this invention.

EXAMPLES

The following examples demonstrate the embodiment of the present invention as described above.

Example 1

To investigate the complimentary nature of HIFU with immunotherapy, a HIFU system was designed with a probe that is capable of providing the user with control over the acoustic properties of the ultrasound transmission and sized appropriately for use in the preclinical murine model. The immune system response to the sequential application of both LO-HIFU, followed by one-to-two days later, HI-HIFU was addressed in the animal model.

The modified Sonablate® 500 operates at HI-HIFU with approximate focal spatial peak temporal peak (SPTP) intensities of 1300 to 2000 W/cm$^2$. The HIFU continuous wave of 3 seconds and operating frequency of 4 MHz for the treatment of prostate cancer is used to achieve tissue temperatures in the focal zone of 80° C. to 95° C. The resulting thermal lesions are approximately 3 mm×3 mm×12 mm with a very sharp demarcation with no tissue damage beyond the focal zone.

For LO-HIFU, the pulse duration is in the micro-second to milli-second range with approximate focal intensities (SPTP) of 500 W/cm$^2$ and pulse repetition frequencies (PRF) on the order of 1 Hz. Also to limit temperature elevation, a lower center frequency near 1 MHz is generally employed. Thus, cells experience mechanical agitation while remaining viable.

The model was established by inoculating a murine prostate cancer cell line, RM-1-OT, which was transfected with ovalbumin, on the footpad and flank of C57BU6 mice. HIFU treatment was administered when tumor size reached 3-5 mm in diameter and adverse effects were evaluated 1-2 weeks after the initial treatment. Phenotype of splenocytes and levels of heat shock protein 70 in tumor and serum were analyzed by flow cytometry and ELISA, 24 hours after HIFU treatment. The results of this analysis are shown in FIGS. 18 and 20.

To evaluate the tumor specific immune response, mice were treated three times by HIFU at one week interval and sacrificed one week after last treatment. Frequency of tumor specific T cells was analyzed by IFN-γ, release ELISPOT assay and cytotoxic functions of these tumor reactive T cells were detected by CD107a mobilization assay. Titer of tumor specific antibodies in serum was evaluated by indirect •ELISA assay. Tumor growth curve was generated by measuring three orthogonal tumor diameters at 1-3-day intervals with a vernier caliper.

To establish a model of prostate cancer, C57BU6 mice (n=40) were injected subcutaneously on footpad or flank with 1×705 RM-1-OT tumor cells. About 10 days later, the tumor became palpable (3-5 mm in diameter), whereupon treatment was initiated. The RM-1-OT is derived from a murine prostate cancer cell line, RM-1, but modified to express chicken ovalbumin (OVA) by stable transfection. OVA was used as a model tumor antigen so that the tumor-specific immune response can be monitored easily.

Figure 9:
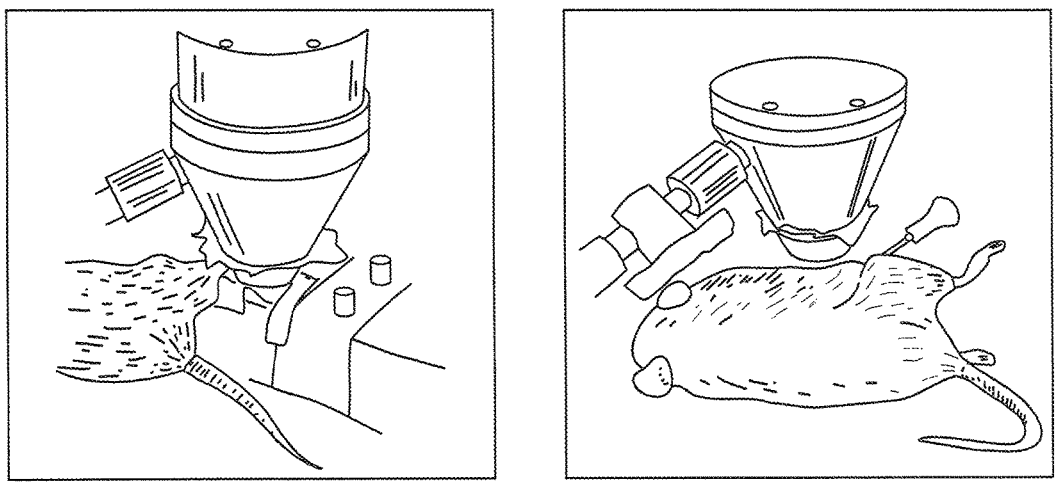
FIG. 9 shows the instrument setup for the HIFU treatment of palpable flank tumors.
Figure 10:
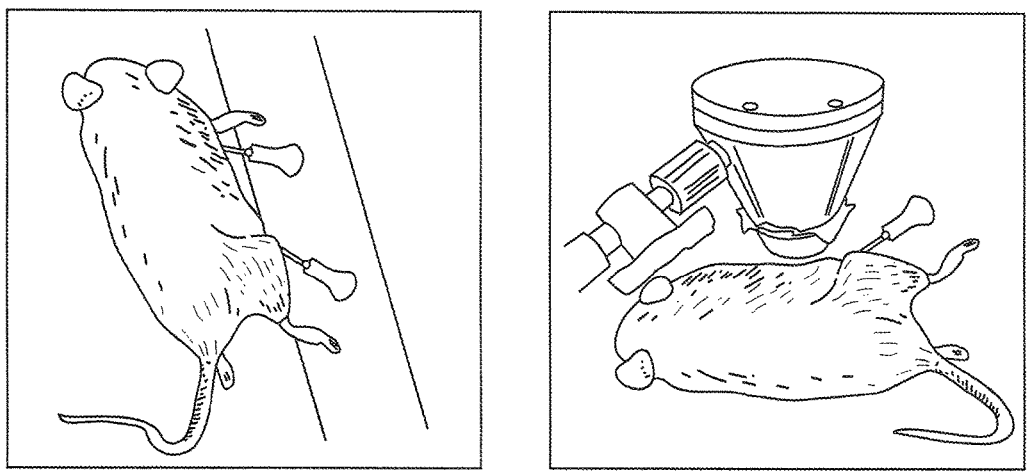
FIG. 10 shows the instrument setup for the HIFU treatment of footpad tumors.

The instrument setup for the HIFU treatment of palpable flank and footpad tumors is shown in FIG. 9 and FIG. 10, respectively. Mice were anesthetized before treatment, and the tumor volume was measured to calculate the grid for alignment. Mice were divided into 4 groups (5 each group) and treated with or without low energy, high energy and combined LO-HIFU and HI-HIFU. In the last combination group, mice were first treated by LO-HIFU and then HI-HIFU was given 24 hours later. The detailed parameters for each kind of treatment are shown in Table 1 and Table 2.

Adverse events were evaluated within 2 weeks after initial treatment and the most frequently observed symptoms were tumor bleeding, ulceration and bone destruction. As shown in table 1, the color of tumor turned to white and red after HI-HIFU treatment and the feet were fell off 1 week later caused by bone fracture. The LO-HIFU did not break the bone on foot but caused tumor ulceration after 1 week as compared with tumor without HIFU treatment. To maximally reduce the occurrence of these adverse symptoms, the parameters for low and high energy HIFU were adjusted and the location of tumor was changed to flank to avoid bone destruction. As shown in table 2, no adverse symptom was found just after HIFU treatment but slight ulceration and bleeding still occurred after 2 weeks.

To further evaluate the effect of HIFU on immune cells, splenocytes were isolated 24 hours after HIFU treatment and the percentages of T cells, B cells, NK cells and Dendritic cells were analyzed by flow cytometry. As shown in table 3, no significant difference was found among these groups indicating there was no adverse effect on immune cells by HIFU treatment. On the contrary, a slight increase in T cells, CD4/8 ratio and CD69+ T cells was found in mice treated with combined LO-HIFU and HI-HIFU.

Figure 11:
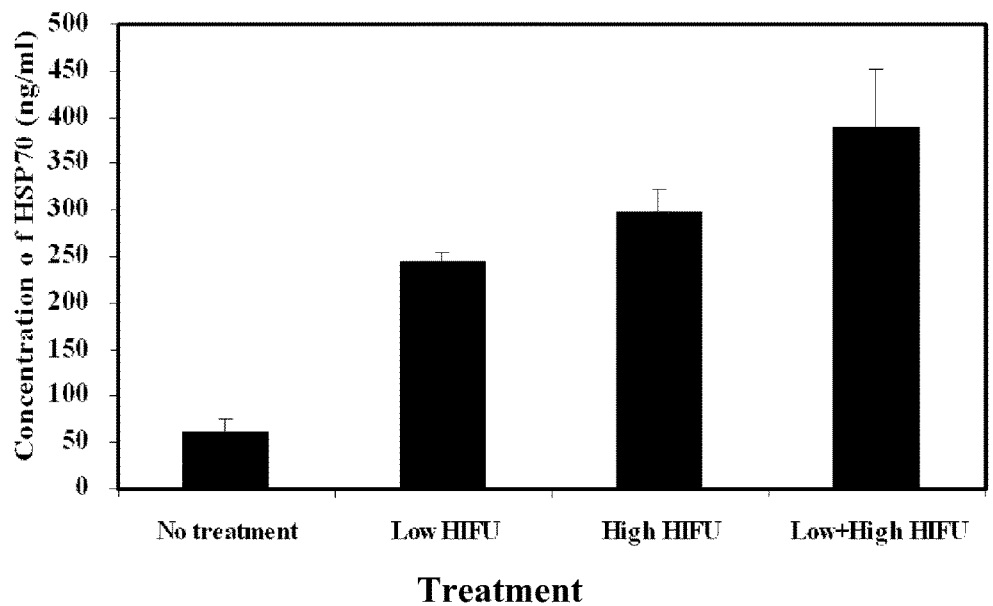
FIG. 11 shows levels of HSP70 in serum and tumor lysate after HIFU treatment.
Figure 11:
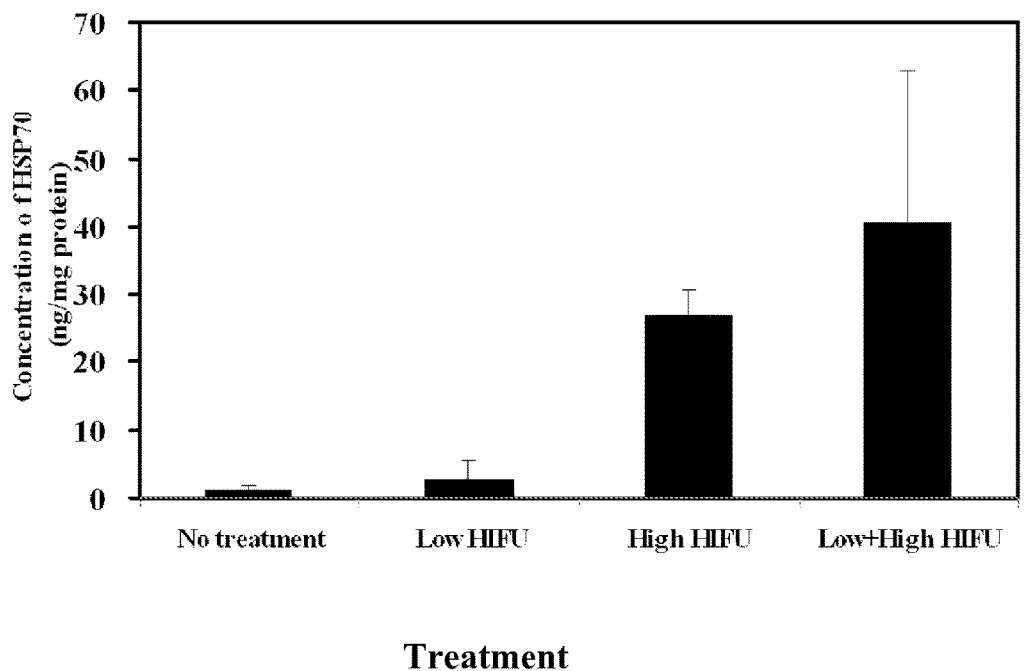

HSP70, a member of heat shock protein family, was found to have potent effect on the enhancement of immune response to tumor. The release of this heat shock protein to the tumor milieu and serum could activate tumor infiltrating and circulating dendritic cells, thus induce a systematic immune response against localize tumor and metastasis. To evaluate whether HIFU could induce HSP70 release in this manner, tumor lysate and serum were collected 24 hours after treatment and levels of HSP70 in these samples were assayed by ELISA using a commercial kit. As shown in FIG. 11, highest level of HSP70 was found in tumor lysate and serum from mice treated by combined LO-HIFU and HI-HIFU. Low and HI-HIFU alone could also induce a detectable HSP release as compared with no treatment group. These results suggest that combined LO-HIFU and HI-HIFU may be the best way to induce a protective immune response against tumor.

Figure 12:
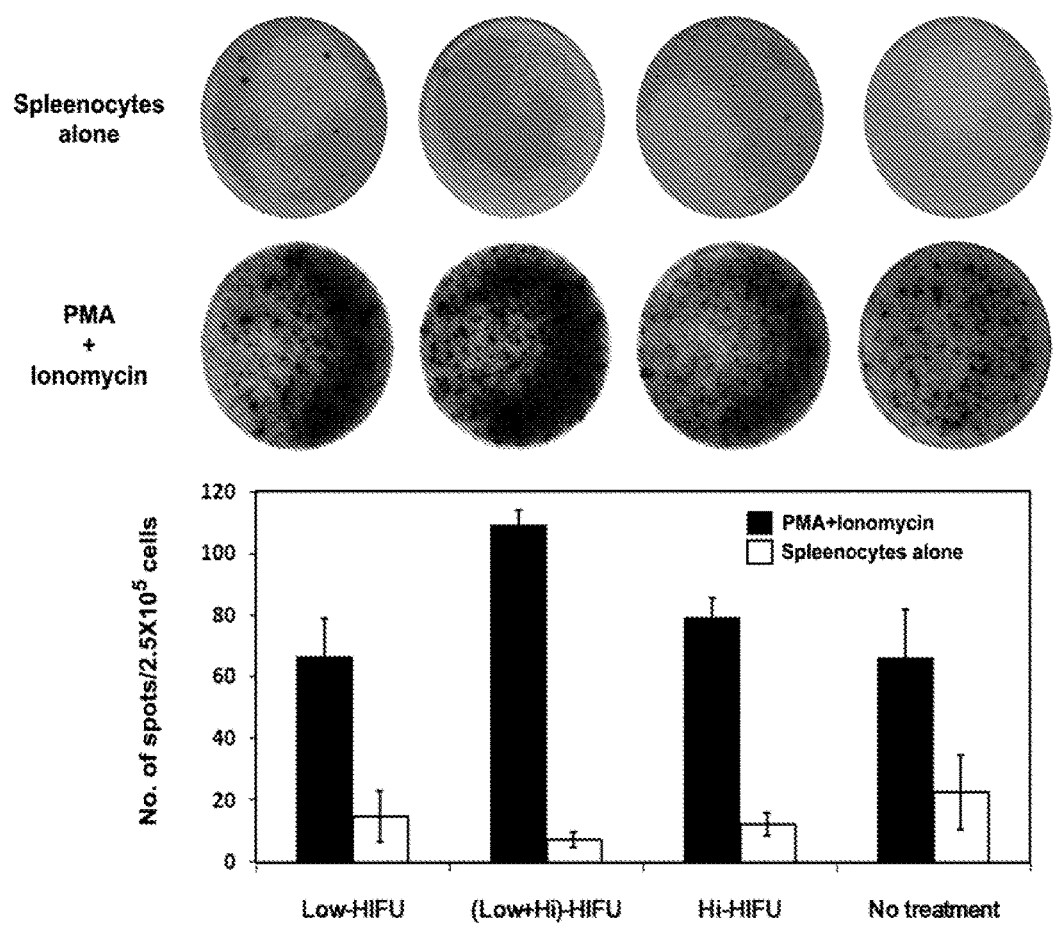
FIG. 12 shows the frequency of IFN-γ releasing cells in splenocytes three days after HIFU treatment.

To evaluate the frequency and magnitude of tumor specific immune response, mice (n=16) were treated once by HIFU and then sacrificed on day 3, 7 and 14. Splenocytes were isolated at each time point and assayed by IFN-γ release ELISPOT. Unfortunately, no tumor specific T cell response was detected at each sample indicating one HIFU treatment maybe not enough to induce a potent immune response in vivo. The only finding in this experiment was that the total number of IFN-γ producing cells was highest in mice treated with combined low and high energy HIFU on day 3 (FIG. 12).

Figure 13:
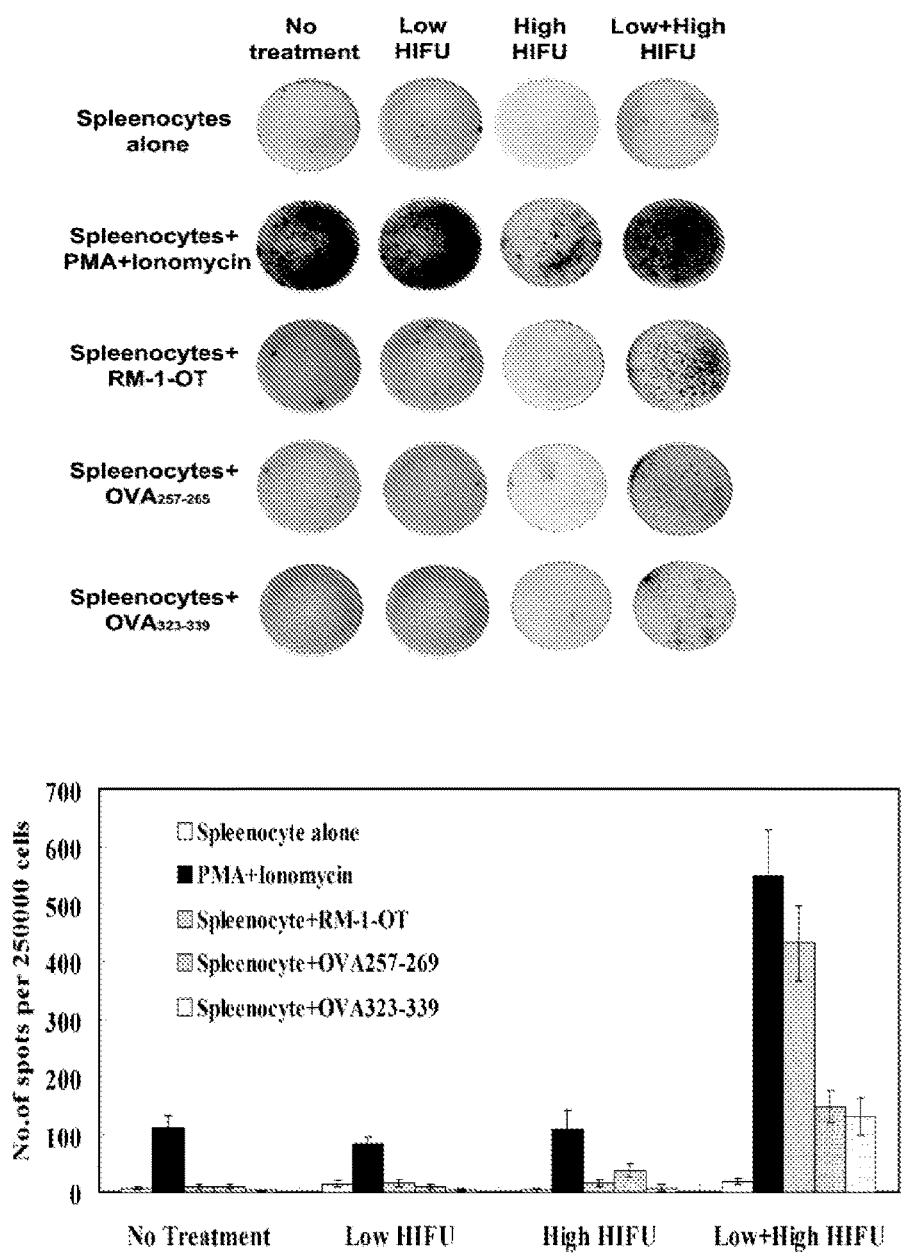
FIG. 13 shows tumor specific T cell response detected by IFN-γ release assay after HIFU treatment.
Figure 14:
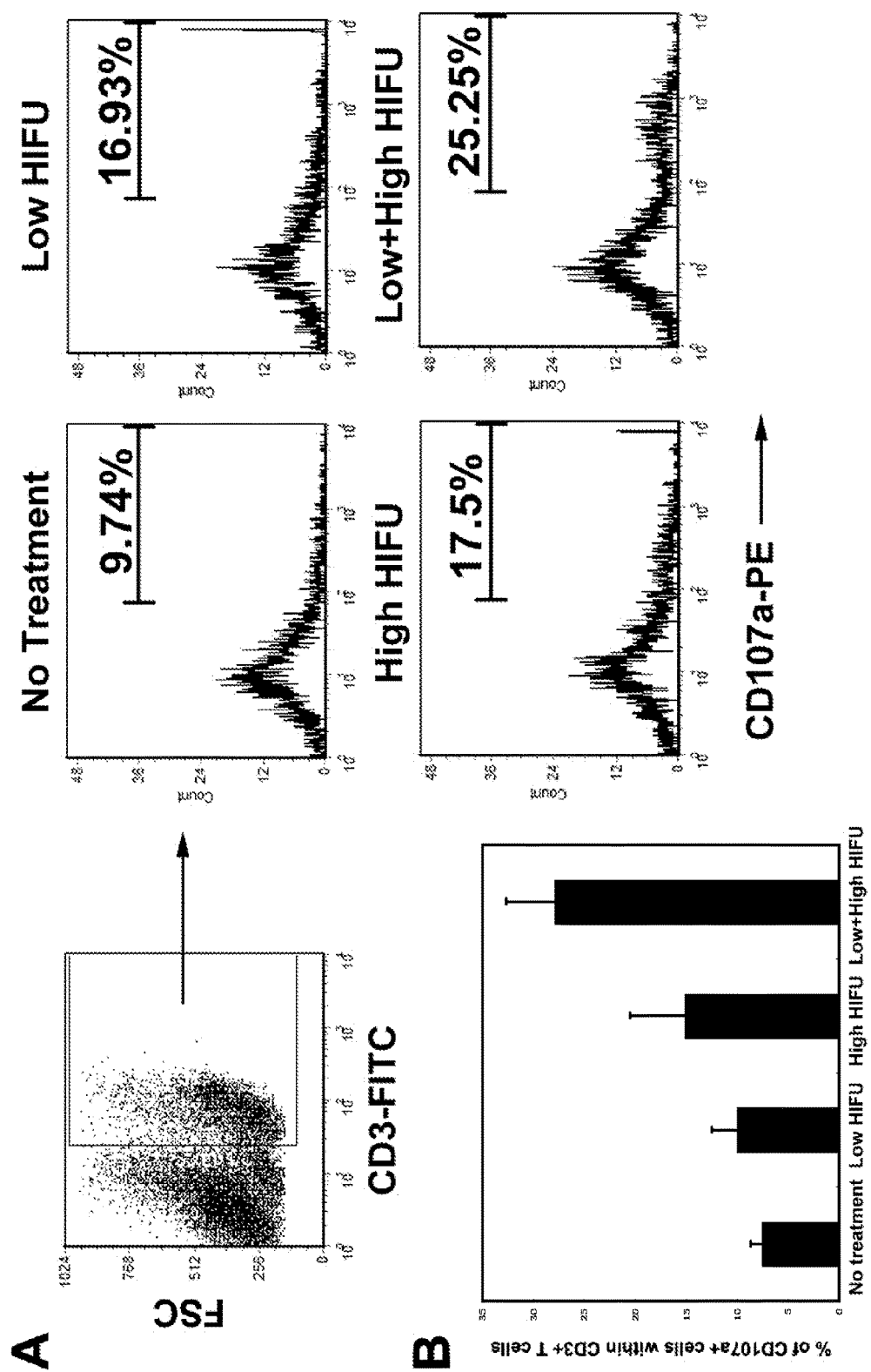
FIG. 14 shows cytotoxic function of tumor reactive T cells detected by CD107a mobilization assay after HIFU treatment.

To enhance the induction of tumor specific immune response, mice (n=16) were treated three times by HIFU at one week interval and sacrificed one week after last treatment. Frequency of tumor specific T cells in splenocytes was analyzed by IFN-γ release ELISPOT assay and cytotoxic functions of these tumor reactive T cells were detected by CD107a mobilization assay. As shown in FIG. 13, potent RM-1-OT specific response was detected in mice treated with combined LO-HIFU and HI-HIFU and this response was also found to be specific to both the MHC class I restricted peptide, OVA257 269 and MHC, class II restricted peptide, OVA323-339. In contrast, no significant immune response was detected in mice treated with LO-HIFU and HI-HIFU alone. FIG. 14 shows the frequency of cytotoxic T cells in mice treated with and without HIFU. Unlike the results from ELISPOT assay, tumor specific CD107a+ T cells could be found in almost every mouse splenocytes even without any treatment But the highest percentage was still found in mice treated with combined LO-HIFU and HI-HIFU which was consistent with the results from ELISPOT assay. The possible explanation of this discrepancy is that some tumor reactive cytotoxic T cells may not be able to release IFN-γ when they encountered tumor cells.

Figure 15:
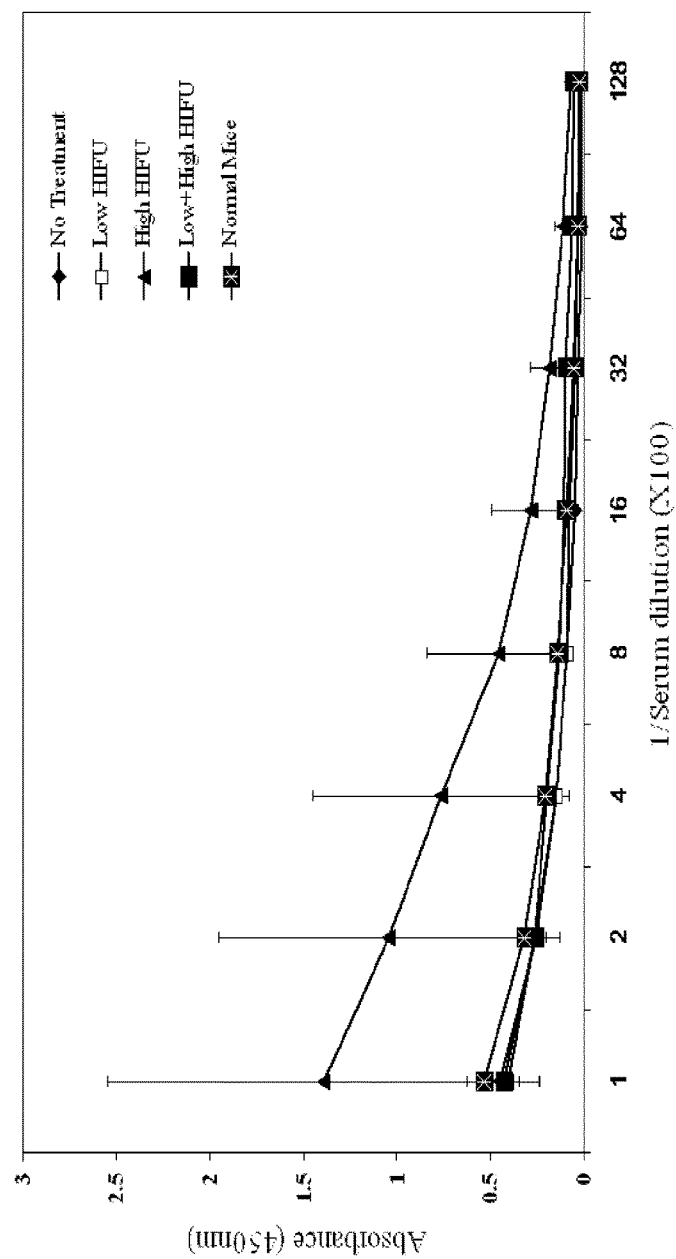
FIG. 15 shows titers of tumor specific antibodies in serum after HIFU treatment.

Beside cellular immune response, HIFU was also found to induce humoral immune response against tumor. Interestingly, the tumor specific antibodies could only be detected in serum from mice treated with HI-HIFU (FIG. 15). The titors of tumor specific antibodies in the other 3 groups were similar as normal mice without any treatment.

Figure 16:
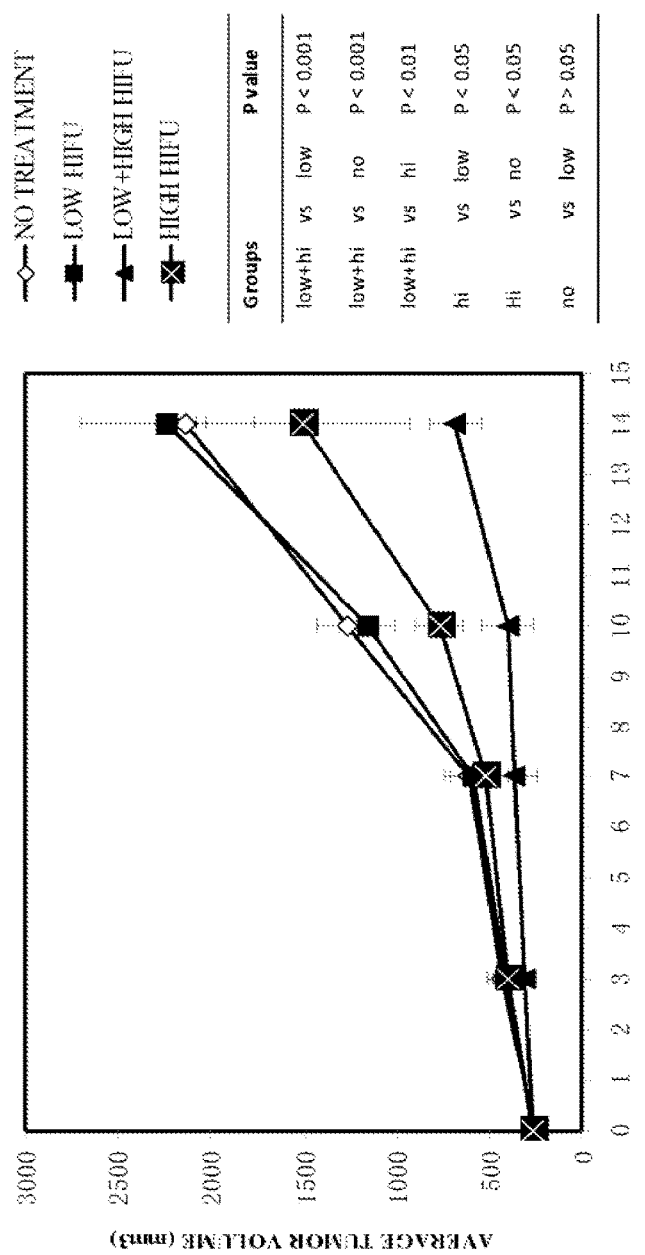
FIG. 16 shows delayed tumor growth after LO-HIFU followed by HI-HIFU.

To evaluate the therapeutic effect of HIFU treatment on tumor, a tumor growth curve was generated by measuring the tumor volume at 1-3-day intervals with a vernier caliper. As shown in FIG. 16, significant tumor retardation was found in mice treated with HI-HIFU and combined LO-HIFU and HI-HIFU. This result correlated with the cellular and humoral tumor specific immune response observed in these mice and may provide a strong evidence for linking HIFU with immune regulation.

Example 2

The immune system response in patients is amplified as follows. This model involves the sequential application of both LO-HIFU, followed by one-to-two days later, HI-HIFU.

The Sonablate® 500 operates at HI-HIFU with approximate focal spatial peak temporal peak (SPTP) intensities of 1300 to 2000 W/cm$^2$. The HIFU continuous wave of 3 seconds and operating frequency of 4 MHz for the treatment of prostate cancer is used to achieve tissue temperatures in the focal zone of 80° C. to 95° C. The resulting thermal lesions are approximately 3 mm×3 mm×12 mm with a very sharp demarcation with no tissue damage beyond the focal zone.

For LO-HIFU, the pulse duration is in the micro-second to milli-second range with approximate focal intensities (SPTP) of 500 W/cm$^2$ and pulse repetition frequencies (PRF) on the order of 1 Hz. Also to limit temperature elevation, a lower center frequency near 1 MHz is generally employed. Thus, cells experience mechanical agitation while remaining viable.

The application of LO-HIFU to a tumor causes the release of cellular material from tumor cells within the tumor. The patient's immune response to the tumor cells is stimulated by using several immunotherapy techniques that utilize the cellular material. These immunotherapy techniques involve delivering to the patient an effective amount of a composition that stimulates the immune system of the patient. The composition may be an anti-tumor vaccine, such as an autologous tumor cell vaccine. Alternatively, the composition may be an immunomodulatory molecule. Preferably the molecule is a cytokine. Such cytokines include, but are not limited to, lymphokines, interleukins and chemokines. The cytokine is a dendritic cell stimulating cytokine, G-CSF. G-CSF is commercially available as Neulasta® and as Neupogen®. The maximum amount of Neulasta® that can be safely administered in single or multiple doses has not been determined. Single doses of 300 mcg/kg have been administered SC to 8 normal volunteers and 3 patients with non-small cell lung cancer without serious adverse effects. These subjects experienced a mean maximum ANC of 55×10$^9$/L, with a corresponding mean maximum WBC of 67×10$^9$/L. The absolute maximum ANC observed was 96×10$^9$/L with a corresponding absolute maximum WBC observed of 120×10$^9$/L. The duration of leukocytosis ranged from 6 to 12 days. Leukapheresis should be considered in the management of symptomatic individuals. The maximum tolerated dose of Neupogen® has not been determined. Efficacy was demonstrated at doses of 4 to 8 mcg/kg/day in the phase 3 study of nonmyeloablative chemotherapy. Patients in the BMT studies received up to 138 mcg/kg/day without toxic effects, although there was a flattening of the dose response curve above daily doses of greater than 10 mcg/kg/day.

The release of the dendritic cell-stimulating cytokines produce dendritic cells in order to prepare the immune system to be receptive to the cellular material disbursed by the HIFU treatment. The HIFU induces heat shock proteins in tumor cells, which are released in the blood after HIFU treatment of solid tumors. The heat shock proteins bind to intratumoral peptides, and spontaneous release of heat shock proteins from HIFU-treated tumor cells provide a source of tumor antigen presentation by circulating dendritic cells. The cellular material is uptaken by the dendritic cells. The tumor antigen-loaded dendritic cells migrate into the lymph nodes. The heat shock proteins released in the blood after HIFU treatment of tumor cells provide the "danger" signal to the dendritic cells and also provide a source of comprehensive tumor-derived peptides for efficient antigen presentation.

In the lymph nodes, maturation of the dendritic cells occurs. For example, CD40L provides signals for dendritic cell maturation and thereby eliminates the need of CD4 T cells. In another example, secondary lymphoid chemokines (SLCs) assist in the anti-tumoral immunity. Sequential use of T lymphocyte-stimulating cytokines induces a strong immune response. Further, IL-2 amplifies the tumor-specific cytotoxic T lymphocytes and IL-15 induces a strong memory T cell response.

As a result, cytotoxic T lymphocytes proliferate and destroy other tumor cells. Thus, HIFU-treated tumor cells serve as an in situ tumor vaccine and induce a strong tumor-specific immune response to eradicate distant micrometastases in recurrent solid tumors.

Although the invention has been described in detail with reference to certain illustrated embodiments, variations and modifications exist within the spirit and scope of the invention as described and defined in the following claims.

The invention claimed is:

1. A method of inhibiting tumor growth in a patient, the method comprising a step of subjecting a tumor of the patient to low energy, high intensity focused ultrasound (LO-HIFU) followed after 1-7 days by a step of subjecting the tumor to high energy, high intensity focused ultrasound (HI-HIFU) in an amount effective to inhibit tumor growth in a patient, wherein the step of subjecting the tumor of the patient to LO-HIFU followed by the step of subjecting the tumor to HI-HIFU is more effective in inhibiting tumor growth than administration of either LO-HIFU alone or HI-HIFU alone.

2. The method of claim 1, wherein HI-HIFU is administered to the patient 1-2 days after administration of LO-HIFU.

3. The method of claim 1, wherein HI-HIFU applies power in the amount of about 1.3 to 2.0 KW per cm$^2$.

4. The method of claim 1, wherein HI-HIFU has an operating frequency of about 1.0 to 5.0 MHz.

5. The method of claim 1, wherein HI-HIFU has an operating frequency greater than about 20 KHz and less than about 100 MHz.

6. The method of claim 1, wherein LO-HIFU applies power in the amount of about 0.5 KW per cm$^2$.

7. The method of claim 1, wherein LO-HIFU applies energy in the amount of about 0.01 to 3.0 KW-seconds per cm$^2$.

8. The method of claim 1, wherein LO-HIFU operates with a pulse having a duration of about 0.01 to 1.0 seconds with pulse repetition frequencies of about 0.5 to 5.0 Hz.

9. The method of claim 1, wherein LO-HIFU operates with repetition frequencies of about 0.5 to 30.0 Hz.

10. The method of claim 1, wherein HI-HIFU operates with repetition frequencies of about 0.5 to 30.0 Hz.

11. The method of claim 1, wherein LO-HIFU is administered at a dose that LO-HIFU treatment, in the absence of HI-HIFU treatment, is ineffective in inhibiting tumor growth, and wherein the step of subjecting the tumor of the patient to LO-HIFU followed by the step of subjecting the tumor to HI-HIFU is more effective in inhibiting tumor growth than administration of HI-HIFU alone.

\* \* \* \* \*